United States Patent [19]

Gama

[11] Patent Number: 4,900,254
[45] Date of Patent: Feb. 13, 1990

[54] UNIVERSAL ARTICULATOR

[76] Inventor: Jose M. Gama, Conde de Linhares 809, Bairro Cidada Jardim, Belo Horizonte, Minas Garais, Brazil

[21] Appl. No.: 137,438

[22] Filed: Dec. 23, 1987

Related U.S. Application Data

[63] Continuation-in-part of Ser. No. 937,224, Dec. 3, 1986, abandoned.

[30] Foreign Application Priority Data

Oct. 15, 1986 [BR] Brazil .................................. 6601914

[51] Int. Cl.⁴ ............................................. A61C 11/00
[52] U.S. Cl. ......................................... 433/65; 433/57; 433/60; 433/54
[58] Field of Search ........................ 433/56, 64, 59, 60, 433/68, 69, 54, 55, 57, 58, 61, 62, 63, 65, 67, 66

[56] References Cited

U.S. PATENT DOCUMENTS

| | | | |
|---|---|---|---|
| 1,368,408 | 2/1921 | Needles | 433/59 |
| 2,521,599 | 9/1950 | Neil | 433/59 |
| 4,330,275 | 5/1982 | Gama | 433/54 |
| 4,412,822 | 11/1983 | Blechner | 433/54 |
| 4,417,873 | 11/1983 | Kulas | 433/54 |
| 4,537,574 | 8/1985 | Clark | 433/69 |

Primary Examiner—Robert P. Swiatek
Assistant Examiner—Adriene J. Lepiane
Attorney, Agent, or Firm—Ostrolenk, Faber, Gerd & Soffen

[57] ABSTRACT

A universal articulator for prosthodontic use includes upper and lower frames with respective horizontal branches. The rear end of the upper frame has inclined wings with slots. The front end of the lower frame has an incisal tray that is inclined. An incisal pin extends from the incisal tray to the upper frame. Articulator pins extend from the lower frame into the upper frame slots. The articulator pins are in different length pairs and the incisal pins are of different lengths and the pins are substituted for accomplishing adjustable spacing between the horizontal branches of the upper and lower frames which are held parallel and horizontal. A dental plaster supporting dental plate is removably supportable on and removable from one or each of the branches by an attachment element easily removed. Alternatively, dental plaster supporting retaining pins extend across the frames.

13 Claims, 8 Drawing Sheets

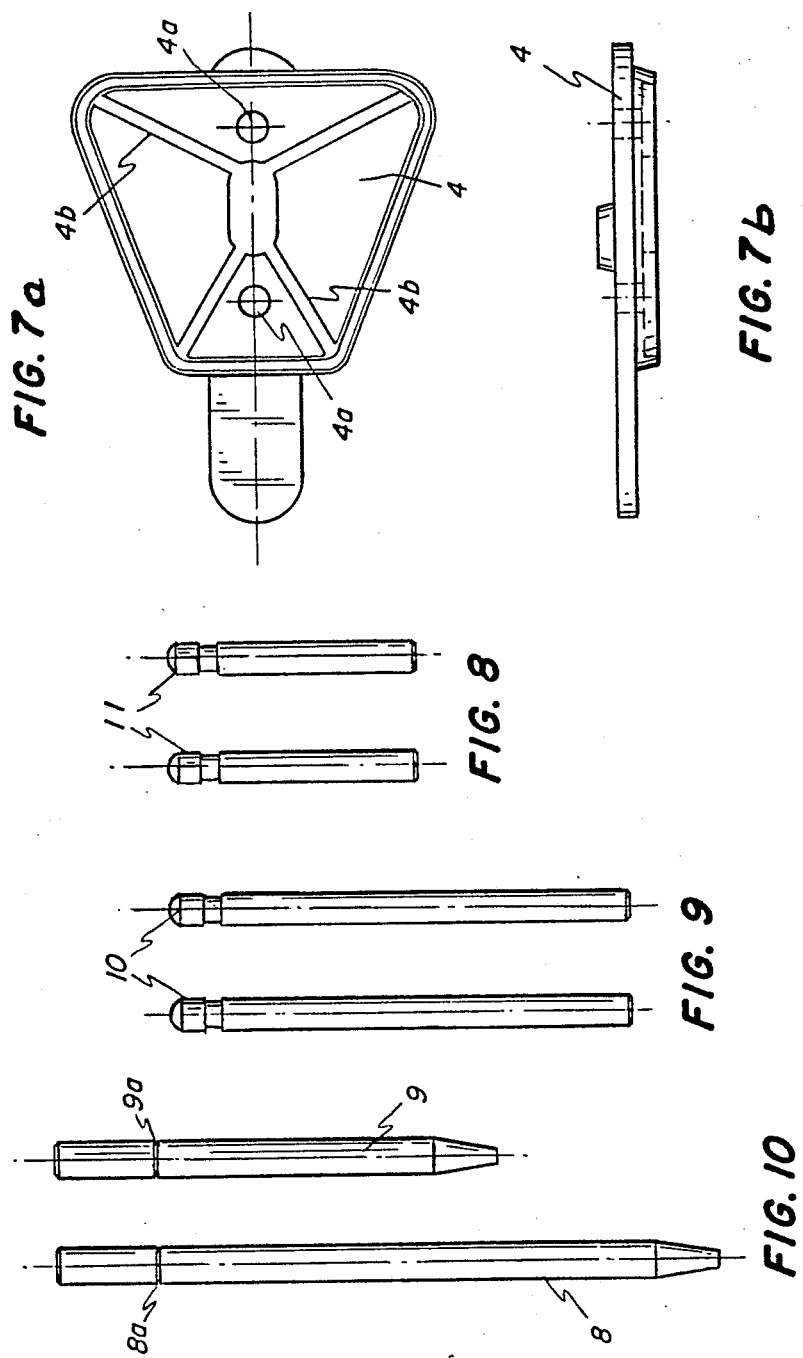

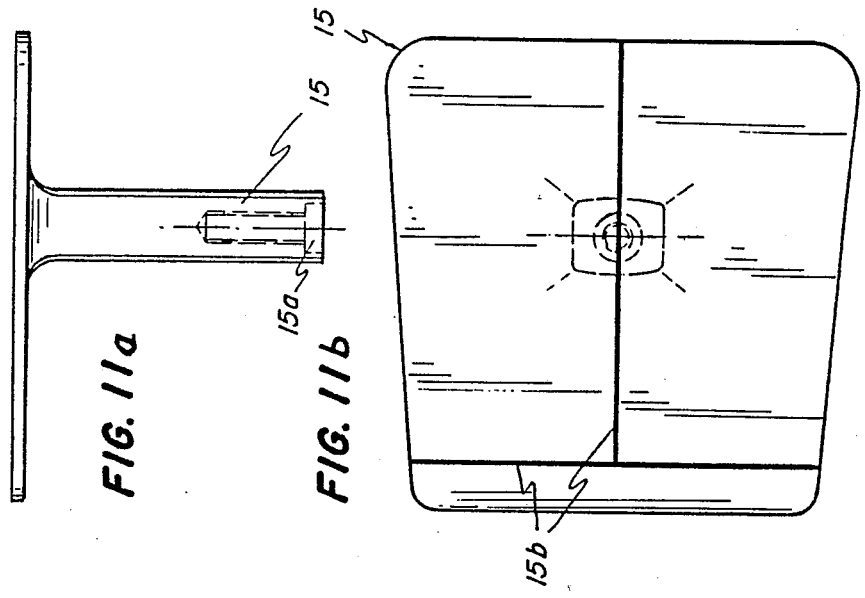
FIG. 11a
FIG. 11b
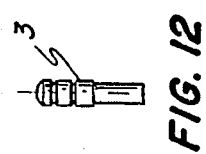
FIG. 12
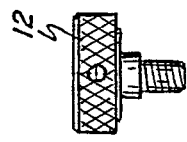
FIG. 13
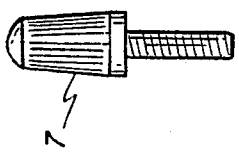
FIG. 14
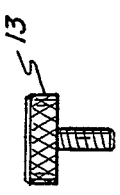
FIG. 15
FIG. 16
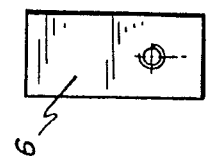
FIG. 17

4,900,254

UNIVERSAL ARTICULATOR

CROSS REFERENCE TO RELATED APPLICATION

This is a continuation-in-part of Ser. No. 937,224, filed Dec. 3, 1986 and abandoned Jan. 27, 1988.

BACKGROUND OF THE INVENTION

This invention relates to a universal articulator, which makes known odontological articulators more useful. The invention is useful, in the field of dental prosthodontics, for the assembly of partial denture plaster models. The invention is an improvement upon the invention of the inventor hereof in U.S. Pat. No. 4,330,275, "Articulator for Models of Dental Arches". That patent is incorporated herein by reference.

The previous patent shows a single partial articulator enabling only the assembly of partial denture plaster models. The previous patent aimed only at a partial working model fitting. Known articulators are either merely partial apparatus for partial denture working model setting or merely total apparatus aimed just at total denture working models.

The present invention turns the previous partial articulator into a universal articulator which is also useful for total denture plaster models, once it is a new remountable apparatus. The versatility of the new articulator provides important savings of labor, material and working time.

SUMMARY OF THE INVENTION

The universal articulator of the invention is an improvement upon the invention of U.S. Pat. No. 4,330,275, incorporated herein by reference. The articulator has the characteristic of allowing its setting and resetting as a partial apparatus (FIGS. 1, 2) or as a total apparatus (FIGS. 3, 4), providing two differently working articulators in one apparatus. Universal articulator accessories and attachments shown (FIGS. 7 to 17) are interchangeable. The complete kit has all of the fittings which are essential to setting the articulator as a partial one (FIGS. 1, 2).

BRIEF DESCRIPTION OF THE DRAWINGS

FIG. 7a is a plan view and FIG. 7b is a side view of a dental plate for use in the present invention;

FIGS. 8 and 9 respectively show different length sets of articulator pins for use with the articulator;

FIG. 10 shows a set of different length incisal pins for use with the articulator;

FIG. 11a is a side view and FIG. 11b is a top view of a mounting tray for use with the articulator embodiment of FIG. 3;

FIG. 12 is a side view of a retaining pin for the articulator;

FIGS. 13, 14, 15 and 16 show various securement screws of the articulator;

FIG. 17 shows a plate used with a brace of the invention; and

FIG. 18 is a side view of a fragment of the articulator showing a brace used thereon.

DESCRIPTION OF PREFERRED EMBODIMENTS

Figure 1:
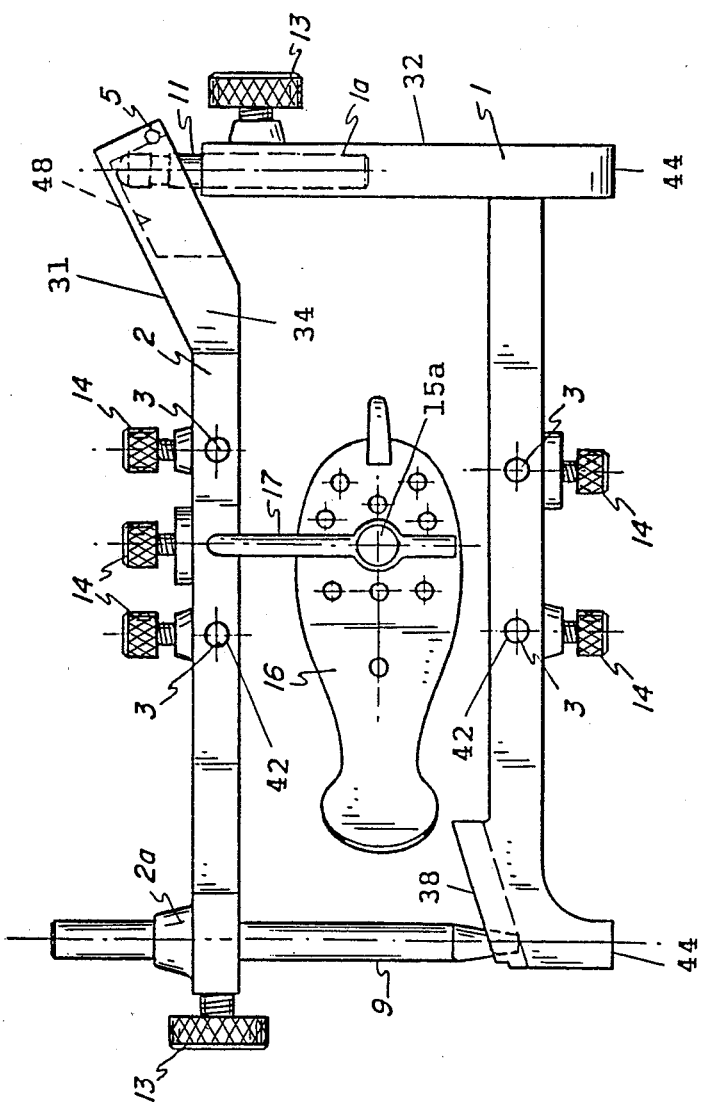
FIG. 1 is a side view of an articulator according to the present invention.

The articulator includes an upper frame 2 which has a horizontal branch and is also comprised of two spaced apart wings 31 (FIG. 2) that are spaced away from the rear end (right in FIG. 1) portion of the central, horizontal branch and extend parallel to it. The articulator also comprises a lower frame 1. The lower frame 1 also has a horizontal branch and has two upright members 32 each ending in an articulator pin 11 having a bulbous end portion, and these end portions enter into the respective slots 34 of the articulator wings 31 above. The wings 31 and their slots 34 are inclined upwardly with respect to the horizontal upper branch of frame 2, are widely spaced and are connected to the main body of the upper branch by arms 36 (FIG. 2). The upward inclination of the wings 31 can vary up around 60°. The upright members or branches 32 of the lower frame 1 are connected to the horizontal branch of the lower frame by arms similar to arms 36. In the front (left in FIG. 1) portion of lower horizontal branch 1, an incisal tray 38 is provided. It has an inclination of about 30° as shown. The inclination can vary at an angle between about 5° and 60°. The horizontal branches of the upper and lower frames 2 and 1 are horizontal, parallel and vertically spaced apart.

Figure 2:
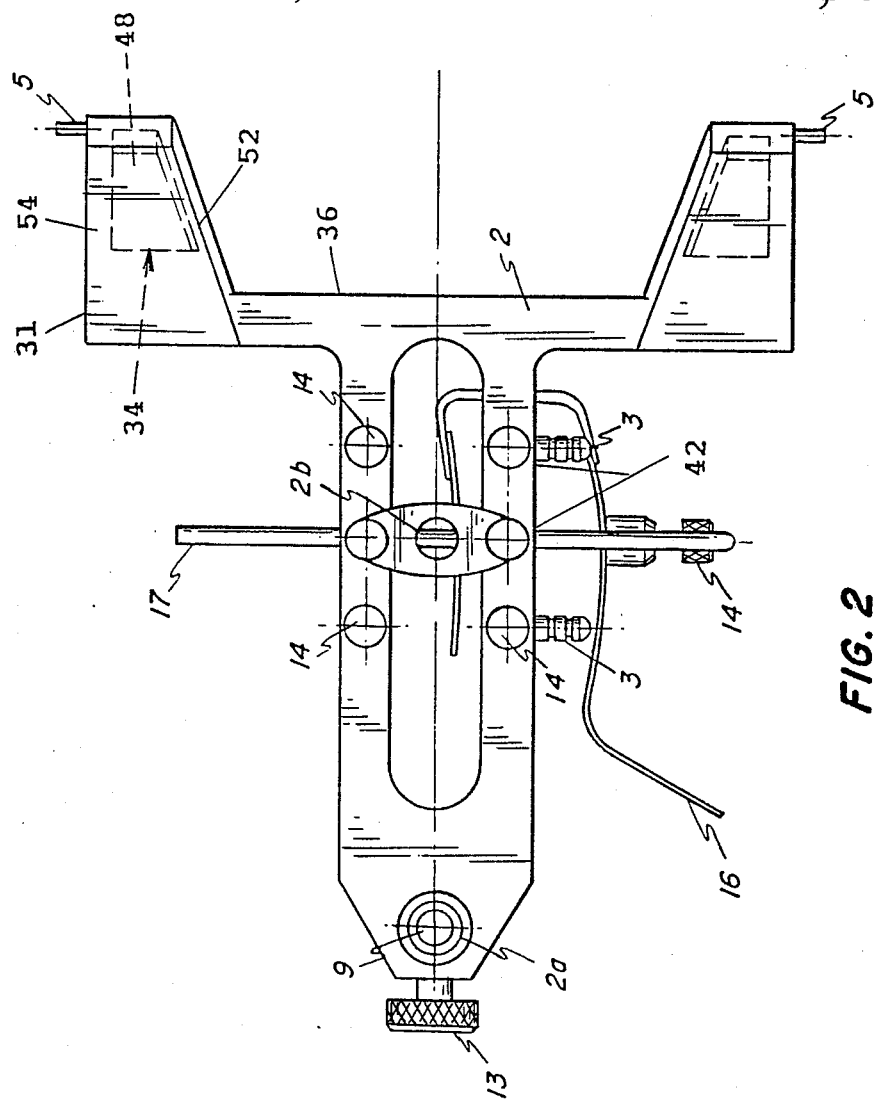
FIG. 2 is a top view of the upper frame of the articulator of FIG. 1, with the additional elements cooperating with the frame as shown in FIG. 1.

The vertically spaced horizontal branches of the upper and lower frames 2 and 1 have respective lateral holes 42, three on each side of the upper horizontal branch of frame 2 and two on each side of the lower horizontal branch of frame 1 (FIG. 1). The upper holes 42 hold retaining pins 3 (FIGS. 1 and 2) and the longer portion of the connecting member 17. The lower holes 42 hold only retaining pins 3. Perpendicular to these holes and coincidental therewith, the holding screws 14 for the retaining pins 3 and the holding and adjusting screw 14 for the connecting member 17 are provided.

The parallelism between the horizontal branches of frames 1 and 2 of the articulator is maintained, in the rear part, by the articulator pins 11 positioned within the articulator slots 34 and, in the front part, by the incisal pin 9 resting on the incisal tray 38, the pins forming a tripod. Each pin 9, which is adjusted and held in place in a hole in frame 2 by the holding and adjusting screw 13, is stabilized with the aid of the stabilizing tapered member 2a.

There are three feet 44 of the articulator positioned beneath the lower horizontal frame 1. They are of such height as to allow free operation of the holding screws 14 of the retaining pins 3 of the lower frame 1.

The slots 34 in the articulator wings 3 are each comprised of a ceiling 48 and four surrounding walls which form the slots 34. The internal walls 52 of slots 34, included for merely aesthetic reasons, can be dispensed with, with no impairment of the motion of the articulator while at the same time maintaining the required angularities that any articulator must have.

The motions of the articulator pins 11 are directed with the aid of the ceilings 48 and the outer walls 54 of the slots 34. The outer walls 54 of slots 34 guide the movements of projection and retroprojection of the upper branch of the articulator on the articulator pins 11 and maintain that movement perfectly aligned by avoiding side movements of the upper piece, which are undesirable during the projection and retroprojection. Such side movements take place when, resting in one of the angles formed by the walls of the slot, a first articulator pin 11 pivots on its axis while the second articulator pin 11 on the opposite side moves frontward (to the left), downward and inward resting simply on the ceiling 48 of the articulator slot 34 and undergoing no side friction. That condition makes the above described movement much smoother than heretofore.

The ceilings 48 and the walls of slots 34, together with the incisal pin 9 and the articular pins 11 when they are in their places, determine the initial position of the articulator in use.

The articulator wings 31 are positioned such that the outward arms 36 that connect the spaced apart articulator wings 31 to the horizontal branch 1 of the upper frame are located in the front (left in FIG. 1), lower part and not in the rear, higher part of the articulator wings 31. The positioning of the arms 36 to the front and lower part of the articular wings 31 changes the center of gravity of the upper frame to a lower, more central location, which provides stability to the articulator.

The retaining pins 3 (FIGS. 1, 2 and 12) hold the plaster and feature three outstanding operating characteristics.

a. As the holes 42 that hold the retaining pins are parallel to each other, such pins, when connected in pairs, higher or lower pairs, or even pairs of higher and lower pins in conjunction, are easily removable when pulled sideways.

b. They have retaining means for holding the plaster, which enable removal of the pins in pairs.

c. They are further provided with a stop, which with the aid of the holding screws of the retaining pins 14, are maintained in their correct positions. On that account, on being removed, the pins can later be put back exactly in their old positions and only in such positions.

The long and the short incisal pins 8 or 9 are provided with a respective mark line in the form of slot 8a or 9a in their upper parts. When that slot is aligned with the upper part of the stabilizing tapered member 2a or the upper part is used as a reference, it establishes the parallelism of the horizontal frames 1 and 2 of the articulator when the articulator pins 10 or 11 are positioned within the articular slots 34 (FIG. 1). The setting screw 13 for pins 8 or 9 is the same as those used for the articulator pins 10, 11.

The connecting member 17 (FIG. 1) comprises a steel wire bent into an "L". Its length has been designed so as to provide better support for the fingers when making the movements with the connecting member, which makes things handier for the operation and also in removing the plaster. As its name indicates, it is the member for the connection of the articulator with the special moulder 16. Its elongated portion fits into the central and lateral hole 42 of the horizontal branch of the upper frame 1 of the articulator and the shorter portion fits into the special moulder 16, when positioned. The connecting member 17 has two movements, one like that of a pendulum and the other sideways. Details of the moulder 16 can be found in prior U.S pat. No. 4,330,275.

Figure 3:
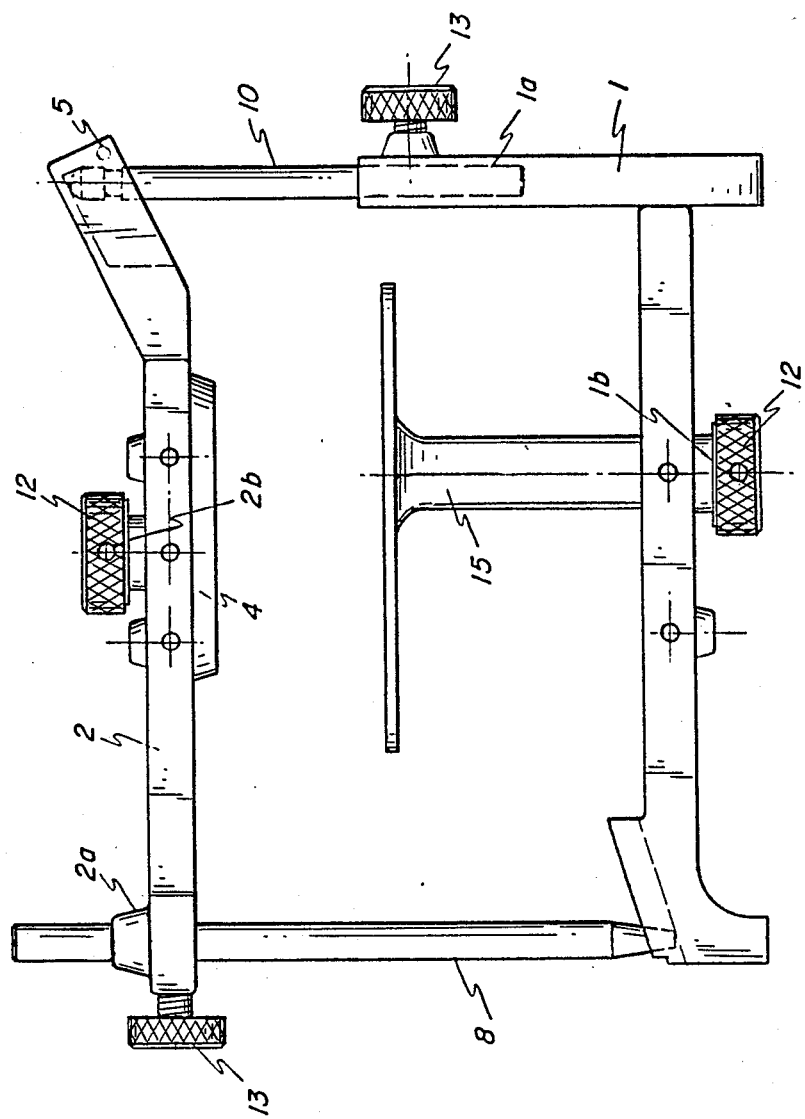
FIG. 3 is a side view of an alternate arrangement of the articulator of FIG. 1.
Figure 4:
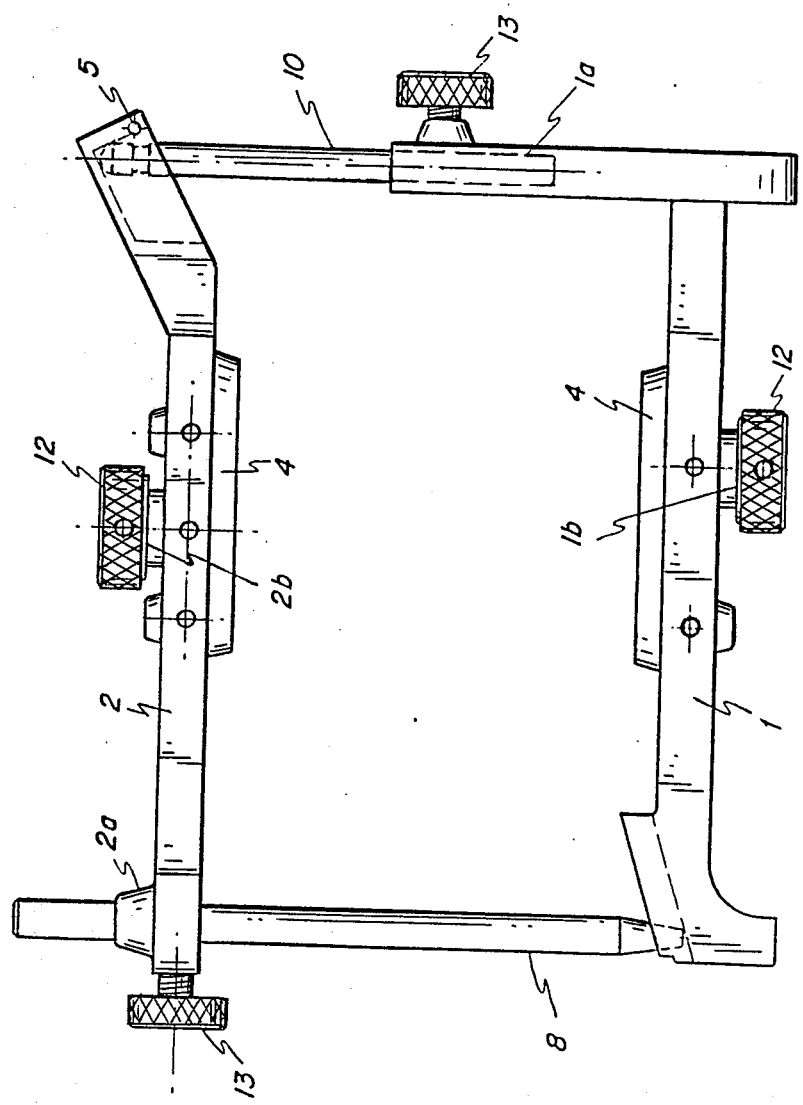
FIG. 4 is a side view of a modified embodiment of the articulator arrangement shown in FIG. 3.
Figure 5:
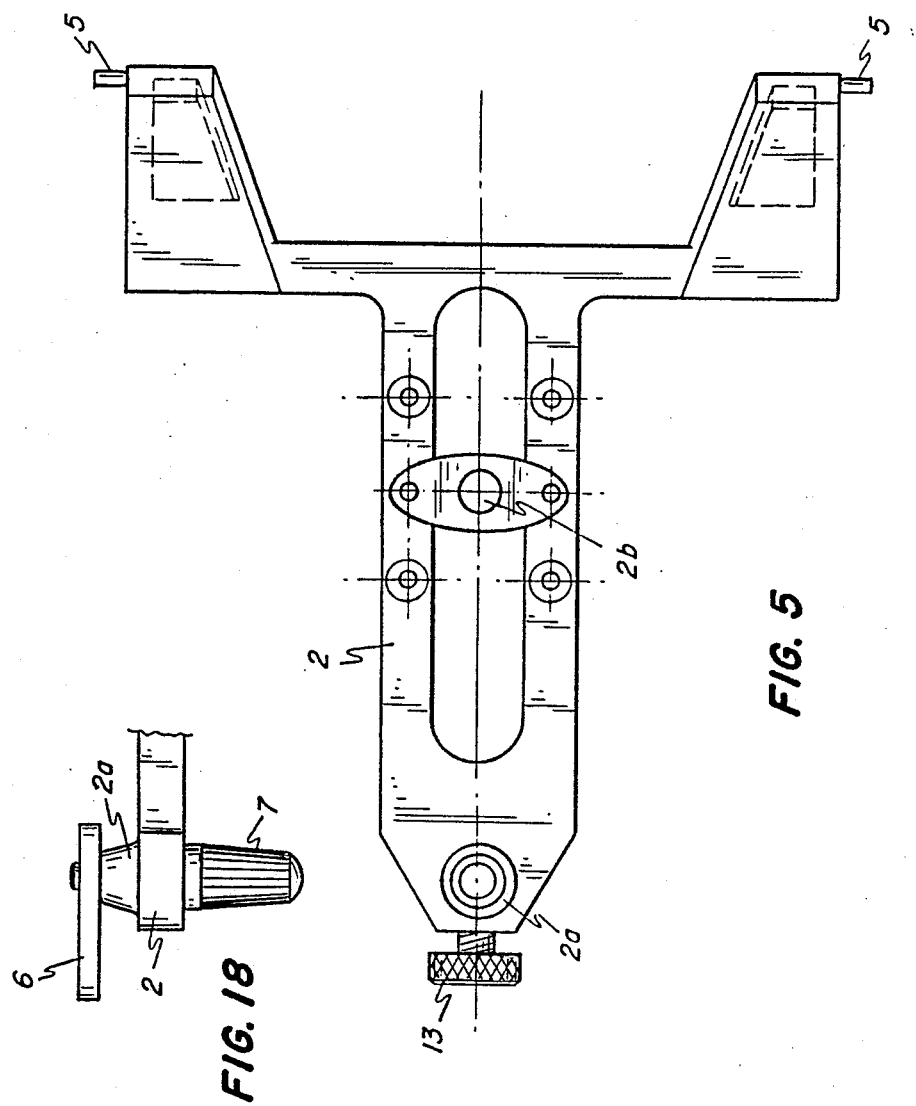
FIG. 5 is a top view of the upper frame of the articulator of FIG. 1 without additional elements.
Figure 6:
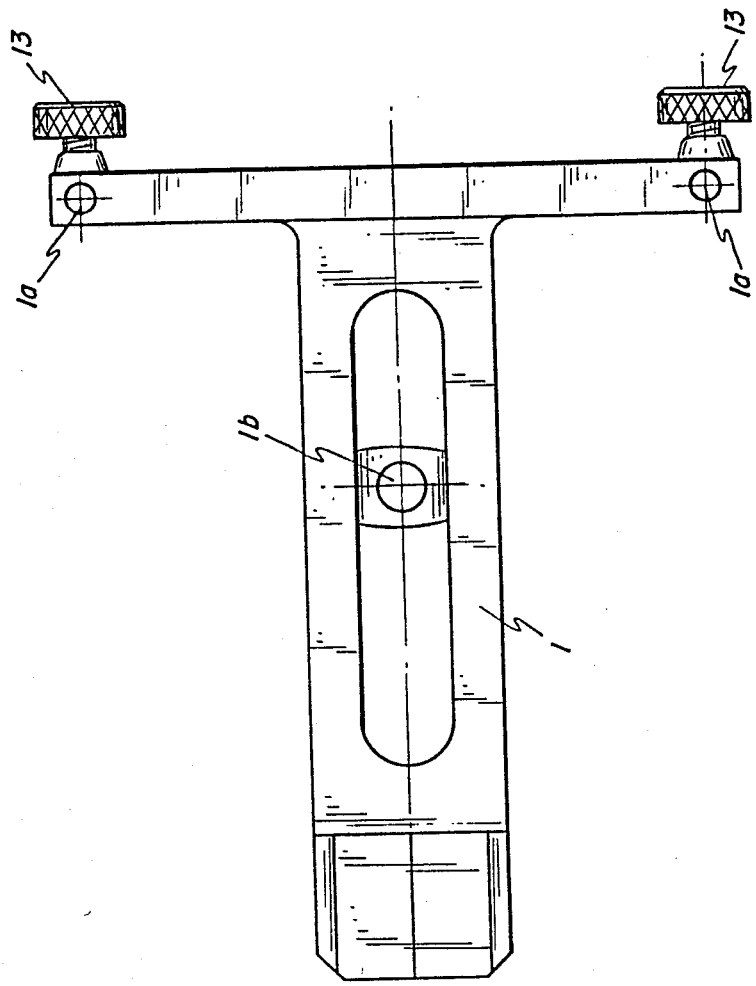
FIG. 6 is a top view of the lower frame of the articulator of FIG. 1.

The universal articulator of the invention enables a prosthodontist to work with many cases in the same period of time by using the retaining pins, which are exchangeable, when the apparatus is set as a partial articulator (FIGS. 1, 2) and by using the dental plates 4, also exchangeable, when the apparatus is set as a total articulator (FIGS. 3, 4). This makes it possible to exchange models. The prosthodontist would have the number of retaining pins 3 or dental plates 4 he needs, e.g. as extra accessories.

An articulator must reproduce the relative position of the upper and lower teeth of the patient with the highest fidelity. Thus, it is essential that the universal articulator have perfect assembly with the face-bow, which is a special prosthodontics apparatus. In order to make the face-bow fitting possible, two lateral pins 5 are added to the articulator wings of the upper frame 2 and an allete brace 6 is located over the incisal pin stabilization cone or tapered member 2a and is screwed through its hole (FIG. 18). The allete brace and the screw are considered integral parts of the exchangeable set.

For technical reasons, a total denture model needs a larger distance between the upper 2 and lower 1 frames. To permit this, the different length articulator pins 10, 11 and the different length incisal pins 8, 9 have been made respectively exchangeable. Therefore, when the longest incisal pin 8 and articulator 10 pin are put into place, the vertical distance between the frames 1, 2 becomes larger. Correspondingly, when the shortest incisal pin 9 and articulator pin 11 are put into place, the distance between frames 1 and 2 becomes shorter. The pins are selected such that the frames 1, 2 must always be kept parallel.

In order to provide a suitable holding system for the articulator pins 10, 11, two new 25 mm deep holes 1a are drilled downwardly through the two lateral vertical bars of the vertical branch 32 of the lower frame 1. These holes 1a also act as stopping points for the articulator pins 10, 11. An orthogonal screw 13 setting system was also added to the posterior portion of the vertical bars, in order to hold the articulator pins 10, 11 in place.

The one short incisal pin 9 and the two short articulator pins 11 are used together for partial works, and these three pins must be exchangeable, respectively, for the one longer incisal pin 8 and the two longer articulator pins 10 to work with total denture models. This practice will keep the frames 2, 1 parallel.

The partial models are attached to the frames 1, 2 with plaster by means of the retaining pins 3, which are proper when the universal articulator is mounted for partial works (FIGS. 1, 2). Orthogonally oriented small screws 14 fix the retaining pins 3 to the upper 2 and lower 1 frames.

The total models are attached to the frames with plaster by means of the dental plates 4 (FIGS. 3 and 4), which are the proper fittings for the total denture model assembly. In FIG. 4, the cooperating plates above and below, at the upper and lower frames, are seen. The two plates are opposite to and face toward each other, and are of the same peripheral shape and would overlie each other.

The retaining pins 3 and the dental plates 4 are designed for better stabilizing the setting of the plaster. The dental plates 4 shown in FIG. 7 include the groove forming retention bars 4b extending across the plates for enabling a better and stabilized setting for attaching plaster and include the disassembling holes 4a which enable a better setting and a faster and more secure total plaster model disassembly, with the use of any kind of instrument (a screwdriver, for instance) inserted through the disassembling holes 4a.

To the upper frame 2 and to the lower frame 1, two respective crossbars 2b, 1b are added, each one provided with a hole, enabling a faster and correct fixation of the dental plates 4. The proper screw 12 is useful for fixation.

The lower crossbar 1b also enables the fitting of a mounting tray 15. The mounting tray 15 has a horizontal plain plate, with two thin locating grooves 15b for centralizing the upper total denture model during its setting. The tray 15 may be used as a substitute for the face-bow, once it enables a relative positioning of the model. For a better assembly to the lower frame 1, a special setting board 15 (FIGS. 1 and 11) has been designed using the mounting elements 15a. It uses the same screw 12 that is used for the dental plates 4.

Although the present invention has been described in connection with a plurality of preferred embodiments thereof, many other variations and modifications will now become apparent to those skilled in the art. It is preferred, therefore, that the present invention be limited not by the specific disclosure herein, but only by the appended claims.

What is claimed is:

1. An odontological articulator comprising an upper frame having and upper branch, a lower frame having a lower branch, and the upper frame branch and the lower frame branch both being substantially horizontal and being and extending parallel to one another;

the upper branch having a rear end portion; a pair of spaced articulator wings spaced outwardly from the rear end portion of the upper branch, the wings also being inclined upwardly at a slight angle from the horizontal upper branch; the wings each having a front part and a rear part, the rear part being in the rear direction with respect to the rear end portion of the upper branch; the upper branch also having a front end portion opposite the rear end portion thereof; means at the front end portion of the upper branch for adjustably receiving and holding an incisal pin;

the lower frame having a rear end portion toward the rear end portion of the upper branch and having a front portion toward the front end portion of the upper branch; a pair of uprights mounted on the lower frame and extending upwardly therefrom toward, and being spaced a distance below, the wing at the upper branch;

an incisal tray attached at the front end portion of the horizontal branch of the lower frame, the incisal tray sloping downwardly forwardly away from the lower branch at an angle from the horizontal;

a plurality of incisal pins, each incisal pin having a bottom end for being received on the downwardly sloping incisal tray, the incisal pin also being adjustably supported in the adjustable holding means therefor in the upper branch;

each wing having an underside facing down toward the lower frame and the wing underside having a slot defined therein for receiving an end of one articulator pin therein;

a plurality of articulator pins, a respective articulator pin being supported on each of the uprights on the lower frame; extending above the upright, each articulator pin having an upper end which is received in the slot of the respective wing above the articulator pin for being retained therein;

a respective arm extending laterally from the rear end portion of the upper branch and connecting to one of the respective wings at the side of the upper branch at the front end of the wing, which is the end portion of the wing that is lower in height with respect to the incline of the wing;

both the articulator pins and the incisal pins being removable from the articulator and being removably secured to the upper branch and to the lower frame of the articulator; the plurality of articulator pins being in pairs of articulator pins, each pair being of a respective length, and the plurality of incisal pins each being of a respective length; the articulator pins of different length being exchangeable on the articulator and the incisal pins of different length being exchangeable on the articulator for enabling the upper branch and the lower frame to be spaced at selected varying distances apart, and a set of articulator pins of a selected length being used with an incisal pin of a respective length selected so that the upper branch and the lower frame remain parallel as the distance between the upper branch and the lower frame is selected.

2. The articulator of claim 1, further comprising a respective dental plate disposed on at least one of the horizontal branches of the upper and lower frames and facing toward the other of the upper and lower frames for receiving and supporting thereon dental plaster.

3. The articulator of claim 2, wherein there is a respective one of the dental plates on each of the upper branch and the lower branch, and the dental plates facing each other.

4. The articulator of claim 3, further comprising a mounting tray supported on one of the branches, and extending a distance toward the other branch and a respective one of the dental plates being defined on the mounting tray, whereby the distance between the plate on the mounting tray and the plate on the other branch is reduced through use of the mounting tray.

5. The articulator of claim 3, further comprising openings extending in the direction across the upper and the lower horizontal branches for receiving retaining pins for plaster, and retaining pins removably replaceable in the openings.

6. The articulator of claim 2, wherein the plate has defined on it groove forming retention bars for enabling better and stabilized setting for attaching plaster.

7. The articulator of claim 2, wherein the dental plate includes assembly and disassembly holes extending through it, the respective horizontal branch to which the plate is to be attached including means placed for cooperating with the holes of the plate, whereby the plate may be rapidly and securely attached and detached from the horizontal branch at the disassembly holes.

8. The articulator of claim 7, wherein the cooperating means on the horizontal branch includes securement holes therethrough and securement means extend through the securement holes to the holes on the dental plates for securing the dental plates to the respective branches.

9. The articulator of claim 1, further comprising openings extending in the direction across the upper and the lower horizontal branches for receiving retaining pins for plaster, and retaining pins removably replaceable in the openings.

10. The articulator of claim 1, wherein each incisal pin includes a height indicating guide thereon for enabling setting of its height with respect to the upper frame.

11. The articulator of claim 1, further comprising a respective lateral pin defined on and projecting laterally outward from each wing.

12. The articulator of claim 11, further comprising an allete brace secured at the upper frame and at the incisal pin.

13. The articulator of claim 12 further comprising interchangeable universal articulator accessories and attachments, including a first set of the accessories and attachments for the articulator to work as an apparatus for assembly of partial denture working models and a second set of accessories and attachments for the articulator to work as an apparatus for assembly of total denture working models.

* * * * *